United States Patent
Olson

(10) Patent No.: US 6,945,098 B2
(45) Date of Patent: Sep. 20, 2005

(54) HYDROCYCLONE WEAR-DETECTION SENSOR

(75) Inventor: Timothy Olson, Tucson, AZ (US)

(73) Assignee: Krebs Engineers Corporation, Tucson, AZ (US)

( * ) Notice: Subject to any disclaimer, the term of this patent is extended or adjusted under 35 U.S.C. 154(b) by 90 days.

(21) Appl. No.: 10/603,679

(22) Filed: Jun. 25, 2003

(65) Prior Publication Data

US 2005/0021246 A1 Jan. 27, 2005

(51) Int. Cl.[7] .............................................. G01N 17/04
(52) U.S. Cl. ........................... 73/86; 136/36; 277/324; 277/919; 324/700
(58) Field of Search .......................... 73/7, 9, 86, 866.5; 138/36; 277/324, 919; 324/512, 519, 522, 525, 537, 700, 754, 755, 71.1, 71.2

(56) References Cited

U.S. PATENT DOCUMENTS

| | | | | |
|---|---|---|---|---|
| 3,078,707 A | * | 2/1963 | Weaver | 73/7 |
| 3,981,621 A | * | 9/1976 | Considine | 417/44.11 |
| 4,092,848 A | * | 6/1978 | Thomas | 73/86 |
| 4,401,941 A | | 8/1983 | Cunningham et al. | |
| 4,642,557 A | | 2/1987 | Ross | |
| 4,646,001 A | * | 2/1987 | Baldwin et al. | 324/700 |
| 4,655,077 A | * | 4/1987 | Purvis et al. | 73/86 |
| 4,780,664 A | * | 10/1988 | Ansuini et al. | 324/700 |
| 4,884,434 A | * | 12/1989 | Satake et al. | 73/7 |
| 4,906,917 A | | 3/1990 | Olness et al. | |
| 5,015,859 A | * | 5/1991 | Uejio | 250/358.1 |
| 5,024,755 A | | 6/1991 | Livsey | |
| 5,121,929 A | * | 6/1992 | Cobb | 277/317 |
| 5,207,409 A | | 5/1993 | Riikonen | |
| 5,266,198 A | | 11/1993 | Vikio | |
| 5,316,320 A | * | 5/1994 | Breaker | 277/611 |
| 5,338,432 A | * | 8/1994 | Agarwala et al. | 205/118 |
| 5,378,991 A | | 1/1995 | Anderson et al. | |
| 5,540,448 A | * | 7/1996 | Heinzen | 277/321 |
| 5,581,019 A | * | 12/1996 | Minor et al. | 73/115 |
| 5,608,376 A | * | 3/1997 | Ito et al. | 340/454 |
| 5,865,971 A | * | 2/1999 | Sunkara | 204/404 |
| 5,977,782 A | * | 11/1999 | Kordecki | 324/700 |
| 6,003,872 A | * | 12/1999 | Nord | 277/317 |
| 6,080,982 A | * | 6/2000 | Cohen | 250/227.11 |
| 6,286,471 B1 | * | 9/2001 | Powell | 123/184.24 |
| 6,366,201 B1 | * | 4/2002 | Hanisko | 340/454 |
| 6,443,016 B1 | * | 9/2002 | Sinelli | 73/810 |
| 6,686,752 B1 | * | 2/2004 | Heumann et al. | 324/700 |
| 2003/0209052 A1 | * | 11/2003 | Ebi | 73/7 |

* cited by examiner

Primary Examiner—Hezron Williams
Assistant Examiner—David A. Rogers
(74) Attorney, Agent, or Firm—Antonio R. Durando; Quarles & Brady Streich Lang LLP

(57) ABSTRACT

Wear-detection sensor has a body of electrically insulating material with an opening through which a flowable substance can pass, and one or more electrical conductors surrounding the opening and adapted to undergo a discernable change in conductivity as the insulating material is worn away by the flowable substance.

27 Claims, 4 Drawing Sheets

US 6,945,098 B2

HYDROCYCLONE WEAR-DETECTION SENSOR

BACKGROUND OF THE INVENTION

1. Field of the Invention

This invention pertains generally to the detection of wear in hydrocyclones and other fluid-flow conduits that are exposed to abrasive substances and, more particularly, to a detection device that functions by monitoring wear on itself.

2. Description of the Prior Art

Hydrocyclones and other conduit components that are exposed to flowing substances are subject to abrasive wear which, if undetected, can lead to failure of the components and of the systems in which they operate.

U.S. Pat. No. 5,024,755 discloses a hydrocyclone with tangential grooves in the outer wall of the separation chamber to create areas of reduced thickness that are designed to perforate and leak as the wall is worn away by the abrasive action of the liquid and particles in the chamber. Thus, the leakage is detected visually and the holes can be sealed with plugs until the chamber is replaced.

U.S. Pat. No. 5,266,198 shows a somewhat similar approach in which a tube is embedded in the wall of the separation chamber. When furrows produced in the wall by the abrasive action reach the tube, it fills with liquid that is detected either visually or electronically to indicate the need to replace the chamber.

Another technique for detecting abrasive wear in a conduit is disclosed in U.S. Pat. No. 4,642,557, where an insulated probe is inserted in a blind hole in the outer portion of the conduit wall. The probe has a tip in electrical contact with the wall at the bottom of the hole, thereby establishing electrical continuity between the probe and the conduit wall. Wear of the conduit down to the tip is detected because it interrupts the continuity between the probe and the wall.

While each of these techniques may have certain utility in specific applications, they also have limitations and disadvantages, such as leakage, which make them less desirable and/or unsuitable for other applications.

SUMMARY OF THE INVENTION

It is, in general, an object of the invention to provide a new and improved wear-detection sensor.

Another object of the invention is to provide a wear-detection sensor of the above character which is particularly suitable for use in hydrocyclones.

These and other objects are achieved in accordance with the invention by providing a wear-detection sensor having a body of electrically insulating material inserted across the wall of a conduit through which a flowable substance is passed, and having one or more electrical conductors adapted to undergo a discernable change in conductivity as the insulating material is worn away by the flowable substance.

According to one embodiment of the invention, the wear-detection sensor consists of a plate with an opening matching the inner geometry of the conduit through which the flowable substance is passed. A plurality of substantially concentric electrical conductors embedded in the body of the device surrounding the opening is used to detect the advancement of wear as each conductor is progressively worn away by the flowable substance.

According to another embodiment of the invention, the wear-detection sensor consists of an insert placed across the wall of the conduit so as to reach the flow channel and contact the flowable substance during operation. A plurality of spaced-apart electrical conductors embedded in the insert is similarly used to detect the progress of wear as each conductor is worn away by the flowable substance with the wall of the conduit.

Various other aspects of the invention will become clear from the description of the invention in the specification that follows and from the novel features particularly pointed out in the appended claims. Therefore, to the accomplishment of the objectives described above, this invention consists of the features hereinafter illustrated in the drawings, fully described in the detailed description of the preferred embodiments, and particularly pointed out in the claims. However, such drawings and descriptions disclose only some of the various ways in which the invention may be practiced.

DETAILED DESCRIPTION OF THE INVENTION

The heart of the invention lies in the idea of inserting a probe across the cross-section and through the inner wall of a conduit so as to expose it to the wear of flowable material. The probe incorporates preferably multiple spaced-apart conductors disposed at progressively greater distances from the inner wall of the conduit, thereby providing multiple sensors to detect wear as each conductor is worn away by the flowable material.

As used in this disclosure, the term "conduit" is intended to refer to any structure capable of sustaining fluid flow, in particular in the form of slurries, such as pipes, ducts, channels, and equipment like hydrocyclones. Therefore, while the description of the invention is based on hydrocyclone and pipe applications, its scope is not intended to be so limited.

Figure 1:
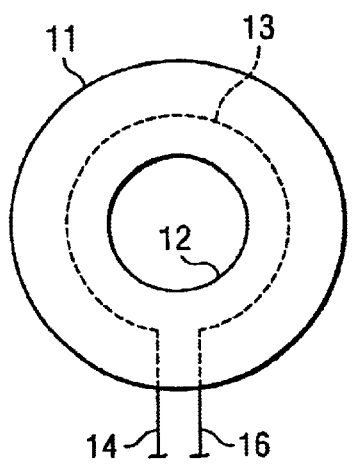
FIG. 1 is a plan view of an annular embodiment of a wear-detection sensor according to the invention.

In the most basic embodiment of the invention, illustrated in FIG. 1, the wear-detection sensor consists of a relatively thin annular body 11 of insulating material, such as urethane or other elastomer, with a central opening 12 designed to substantially match the size and geometry of the inner wall of the conduit for which it is intended. An electrically conductive wire 13 is embedded in the body and disposed concentrically about the opening. Leads 14, 16 provide electrical connections to the end portions of the wire so that its conductivity or continuity can be monitored.

Figure 2:
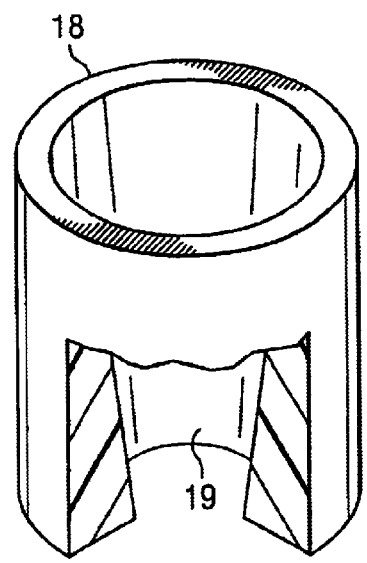
FIG. 2 is a perspective view of the embodiment of FIG. 1 in combination with a partly broken away, unworn apex of a hydrocyclone.

The wear-detection sensor is intended to be placed between two parts which are subject to abrasive wear by a substance flowing through them. In FIG. 2, the device is shown in conjunction with the apex liner 18 of a hydrocyclone. This liner is typically made of a ceramic or rubber material, and the wear-detection sensor is installed so as to form a seal between the discharge end of the apex and a splash skirt or tailpiece (not shown) conventionally connected to it. The apex has a conically tapered passageway 19, and, when new, the inner and outer diameters of the wear-detection sensor are selected to match those at the discharge end of the apex. The conductor is spaced from the opening in the device by a distance corresponding to the permissible wear for the liner.

Figure 3:
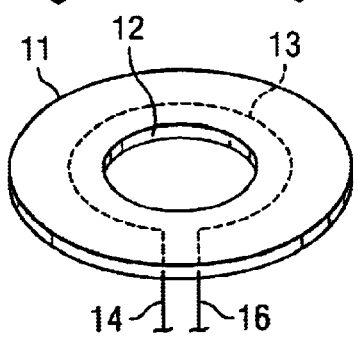
FIG. 3 is a view similar to FIG. 2, showing the device and the apex in a worn condition.
Figure 3:
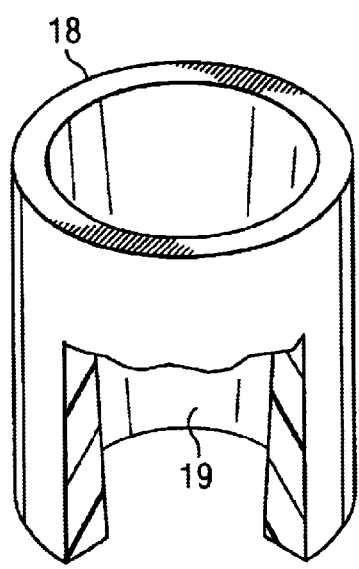
Figure 3:
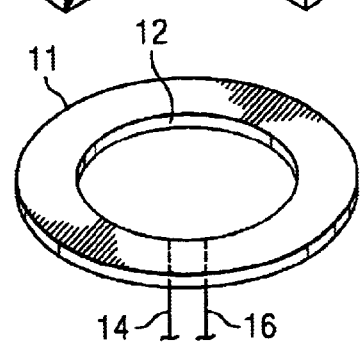

As the inner wall of the liner is worn away by the abrasive action of the slurry passing through it, the body of the wear-detection sensor is likewise eroded away. When the wear reaches the point when the liner needs to be replaced, as determined by the position of the conductor within the body of the wear-detection sensor, the conductor is also eroded away, as illustrated in FIG. 3. Thus, a corresponding change in conductivity or continuity is detected by monitoring an electrical current applied to the conductor.

Figure 4:
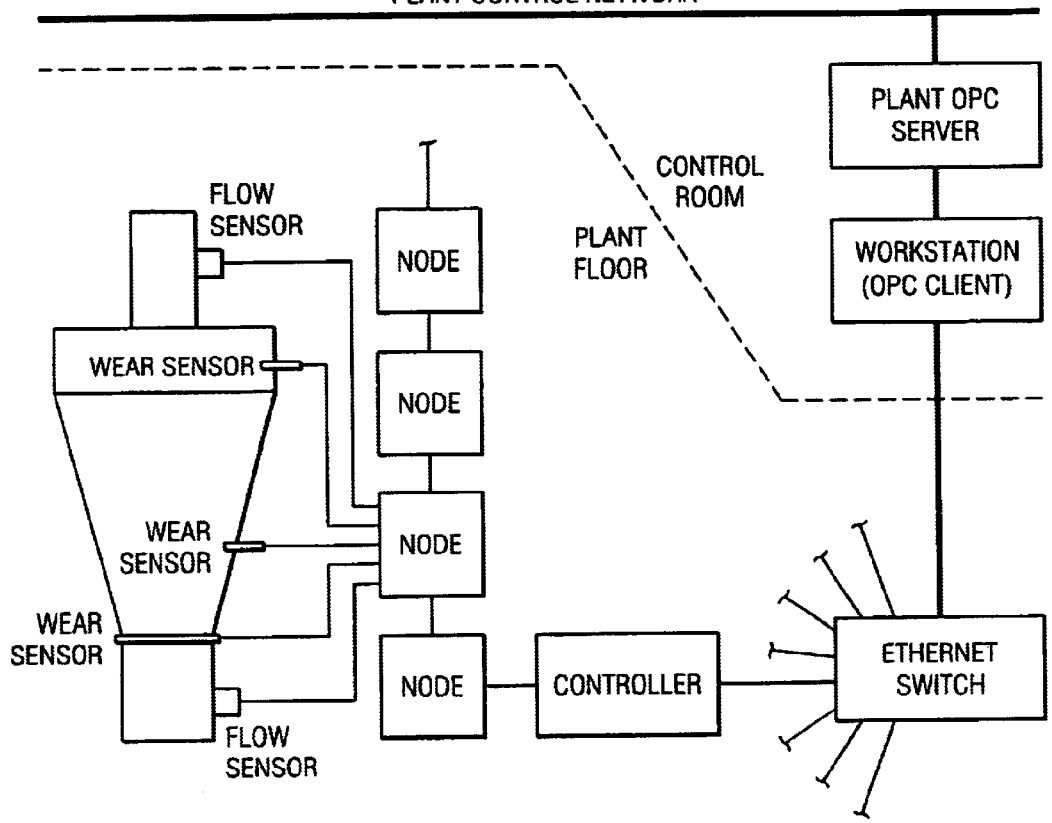
FIG. 4 is a block diagram of a system for monitoring wear with a wear-detection sensor according to the invention.

As illustrated in FIG. 4, one or more wear-detection sensors installed between sections of a hydrocyclone are connected to a control system through a microcontroller node programmed to run and read the sensors, perform data processing, and communicate with higher levels in the network. Since hydrocyclones are typically used in multiple units operating in parallel, the signals to and from each unit are processed by a corresponding node and relayed to a common controller. This, in turn, may be connected via ethernet or otherwise to workstations and a main computer in the plant control network.

Figure 5:
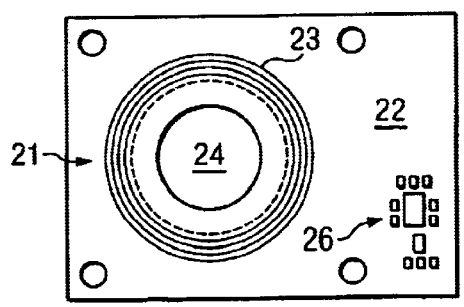
FIGS. 5 and 6 are plan views of additional annular embodiments of a wear-detection sensor according to the invention.

In the embodiment illustrated in FIG. 5, the wear-detection sensor of the invention comprises a printed circuit board 21 having an insulating substrate 22 on which a plurality of conductive rings 23 are formed concentrically about an opening 24. A microprocessor 26 and/or other electronic circuitry is mounted on the board itself and connected to the rings for monitoring conductivity or continuity.

This embodiment permits monitoring of the progress of wear prior to the time the part with which the device is used actually needs to be replaced. In that regard, it will be noted that the rings will wear and lose continuity in succession as the substrate wears away and the opening becomes larger. By monitoring the continuity of the individual rings, the progress of the wear can be determined. In the preferred embodiment of the invention, 18 concentric conductor rings 23 are spaced apart about 0.025 inches, thereby providing wear monitoring over a span of about half an inch.

Figure 6:
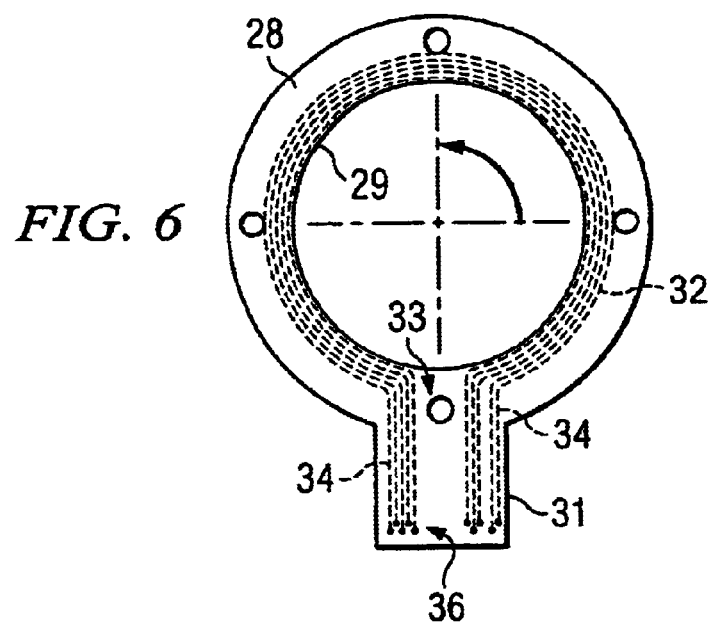

In the embodiment of FIG. 6, the wear-detection sensor has a generally annular body 28 of insulating material with a central opening 29 and a radial tab 31. This device also has a plurality of conductive rings 32 disposed coaxially of the central opening, with gaps 33 in the rings on the side of the opening toward the tab. The end portions of the rings on opposite sides of the gaps are connected to conductors 34 which extend in a generally radial direction to pads or terminals 36 near the outer end of the tab, with the conductors from the inner rings passing through the gaps and between the conductors from the outer rings.

This embodiment can also be constructed in the form of a printed circuit board, with the substrate forming the insulating body and the rings, conductors and pads being formed as unitary structures by a pattern of conductive foil on one or both sides of the substrate.

Figure 7:
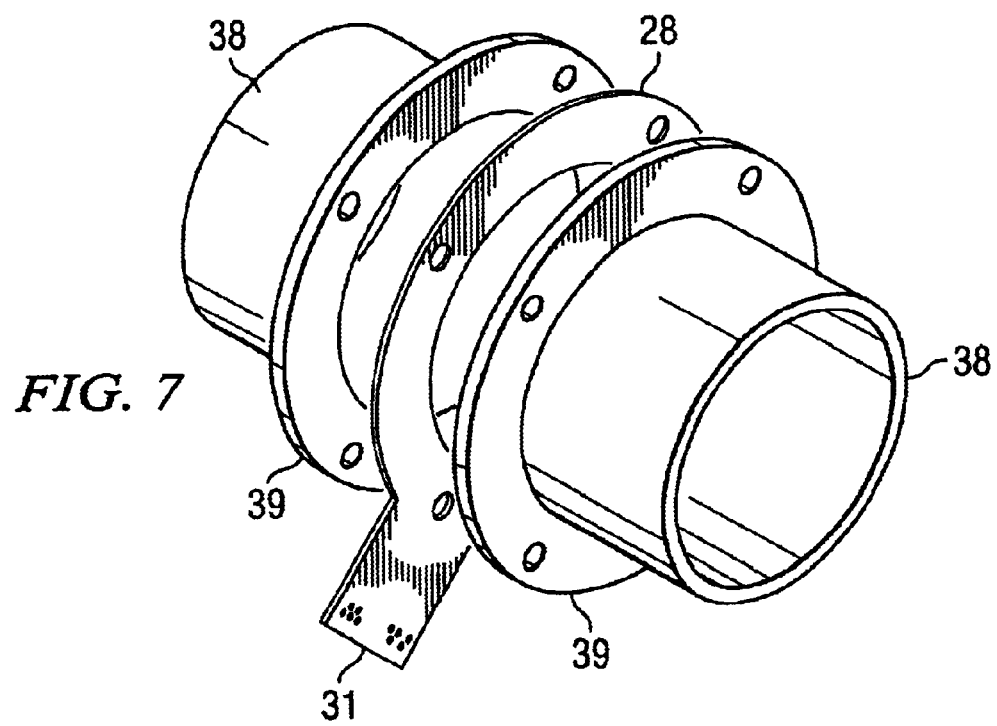
FIG. 7 is a perspective view of the embodiment of FIG. 6 in combination with two flanged pipes.

FIG. 7 illustrates the wear-detection sensor of FIG. 6 mounted within two pipes 38 with annular connecting flanges 39. The device is positioned between the flanges, with the opening in the device aligned with the openings in the pipes. As in the other embodiments, abrasive wear of the inner walls of the pipes is determined by monitoring the conductivity or continuity of the conductive rings in the wear-detection sensor.

Figure 8:
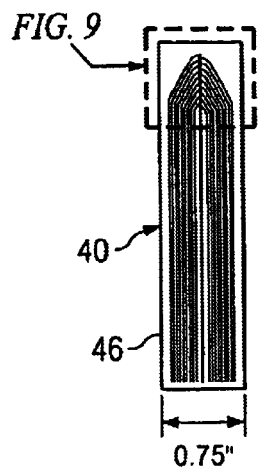
FIG. 8 is a plan view of a tab-insert embodiment of a wear-detection sensor according to the invention.
Figure 9:
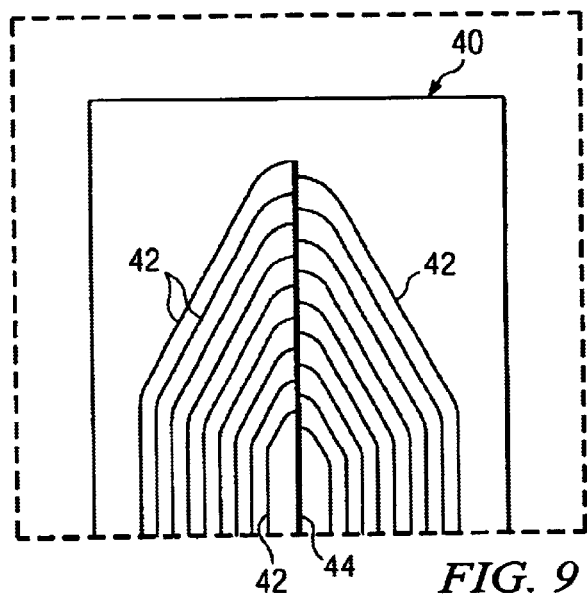
FIG. 9 is an enlarged partial view of the tab insert of FIG. 8.

In yet another embodiment of the invention, the wear-detection sensor is in the form of a tab insert 40, as illustrated in FIG. 8. The insert is designed for radial placement across the wall of a conduit, such as at the junction between segments of pipe or between the cones or a cone and the skirt of a hydrocyclone, so as to reach the inner wall of the conduit and be exposed to the wear and tear of the flowing material. As better seen in the enlarged view of FIG. 9, the insert 40 also includes a plurality of spaced-apart conductors 42 disposed at varying radial distances from the inner wall of the conduit. Each conductor 42 is preferably connected to a common ground conductor 44, thereby providing multiple conductive loops that extend to different radial positions. As in the case of the embodiment of FIG. 6, terminals (not shown in the figure) near the outer end 46 of the tab are available for connection to the monitoring system.

It is understood that any of the above-described wear-detection sensors of the invention can be used in different manners to meet the requirements of particular applications. For example, a plurality of devices can be employed to monitor the wear of the inner lining throughout the length of a hydrocyclone. Inasmuch as a typical hydrocyclone consists of multiple sections connected by flanges, a wear-detection sensor can be installed at each point of connection (as shown in FIG. 4) to measure local wear along the entire length of the equipment.

Figure 10:
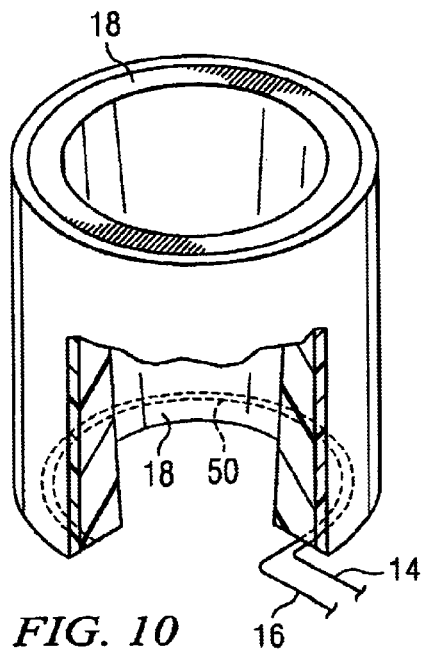
FIG. 10 illustrates a sensor according to the invention embedded in the lining of a hydrocyclone.

As illustrated in FIG. 10, the wear-detector sensor of the invention, in either annular or radial-tab configuration, may be implemented as a structure 50 embedded in the inner lining 18 of the hydrocyclone (or other conduit). In such case, the sensor leads 14,16 are adapted to extend from the lining, preferably between adjoining components, for connection to the monitoring and control system, as illustrated in FIG. 4.

Thus, the invention has been shown to have a number of important features and advantages. It provides an economical and reliable way of monitoring abrasive wear of internal surfaces and determining when parts need to be replaced. In any of the disclosed embodiment, the invention can be easily installed at any point along a conduit where two segments are connected by flanges. Because of its thin profile, the annular embodiment can simply be inserted between connecting flanges. Similarly, the tab-insert embodiment can be pressed against seals between flanges without causing material mechanical stresses of deformations. In addition, because of the redundance provided by the many conductive loops in the preferred embodiments of the invention, they can be installed and function successfully even if they are not perfectly aligned with the inner wall of the conduit. So long as the wear-detection sensor reaches through the inner wall and is exposed to wear, any portion protruding into the flow channel as a result of misalignment is readily worn out and the system may be calibrated so that the remaining conductive loops provide the desired monitoring function.

It is apparent from the foregoing that a new and improved wear-detection sensor has been provided. While it is particularly useful for applications to detect wear in the separation chambers of hydrocyclones, it can be used in numerous other applications as well.

Thus, while the invention has been shown and described in what is believed to be the most practical and preferred embodiments, it is recognized that appropriate deviations can be made within the scope of the disclosure. Therefore, the invention is not to be limited to the disclosed details, but is intended to embrace all equivalent structures and methods.

What is claimed is:

1. A wear-detection sensor comprising a body of electrically insulating material with an opening through which a flowable substance can pass, and an electrical conductor surrounding the opening and adapted to undergo a discernable change in conductivity as the insulating material is worn away by the flowable substance;

wherein the body of insulating material and the conductor are parts of a printed circuit board.

2. The wear-detection sensor of claim 1, wherein the conductor is embedded in the insulating material.

3. The wear-detection sensor of claim 1, wherein the insulating material is urethane.

4. The wear-detection sensor of claim 1, further including signal processing circuitry mounted on the printed circuit board and connected to the conductor.

5. A wear-detection sensor, comprising a body of electrically insulating material with an opening through which a flowable substance can pass, and a plurality of electrical conductors disposed concentrically of the opening and adapted to successively undergo changes in conductivity as the opening increases in size due to abrasive wear of the insulating material by the flowable substance;

wherein the body of insulating material and the conductors are parts of a printed circuit board.

6. The wear-detection sensor of claim 5, together with a monitor connected to the conductors for detecting the changes in conductivity to determine the amount of wear.

7. The wear-detection sensor of claim 5, wherein the insulating material is urethane.

8. The wear-detection sensor of claim 5, further including signal processing circuitry mounted on the printed circuit board and connected to the conductors.

9. A wear-detection sensor comprising a body of electrically insulating material positioned between two parts which carry a flowing substance, with an opening in the body through which the substance can pass, and an electrical conductor surrounding the opening and adapted to undergo a discernable change in conductivity as the insulating material is worn away by the flowing substance;

wherein the body of insulating material and the conductors are parts of a printed circuit board.

10. The wear-detection sensor of claim 9, including at least one additional conductor disposed coaxially about the opening and adapted to undergo a change in conductivity as the insulating material near the additional conductor is worn away by the flowing substance.

11. The wear-detection sensor of claim 9, wherein one of the two parts is the conically tapered separation chamber of a hydrocyclone.

12. The wear-detection sensor of claim 9, wherein one of the two parts is a pipe.

13. The wear-detection sensor of claim 9, wherein the insulating material is urethane.

14. The wear-detection sensor of claim 9, further including signal processing circuitry mounted on the printed circuit board and connected to the conductors.

15. A wear-detection sensor comprising a body of insulating material adapted to be worn away in an outward direction by a substance flowing through a central opening in the body, a ring of electrically conductive material disposed concentrically of the opening and adapted to be worn away with the insulating material, and a gap in the ring between confronting end portions to which electrical connections are made to monitor continuity of the conductive material;

wherein the body of insulating material and the ring of conductive material are parts of a printed circuit board.

16. The wear-detection sensor of claim 15, wherein the insulating material is urethane.

17. The wear-detection sensor of claim 15, further including signal processing circuitry mounted on the printed circuit board and connected to the end portions of the conductive material.

18. A wear-detection sensor comprising a body of insulating material adapted to be worn away in an outward direction by a substance flowing through a central opening in the body, a plurality of concentric rings of electrically conductive material disposed concentrically of the opening and adapted to be successively worn away with the insulating material, and gaps in the rings defining end portions to which electrical connections are made to monitor continuity of the conductive material;

wherein the body of insulating material and the electrically conductive material are parts of a printed circuit board.

19. The wear-detection sensor of claim 18, wherein the gaps are aligned radially on one side of the opening, with radially extending conductors connected to the end portions of the rings and the conductors connected to an inner ring passing through the gap in an outer ring.

20. A wear-detection sensor for a conduit having an opening for passing a flowable substance, comprising a body of electrically insulating material with an electrical conductor adapted to undergo a discernable change in conductivity as the insulating material is worn away by the flowable substance;

wherein the body of insulating material and the conductor are parts of a printed circuit board.

21. The wear-detection sensor of claim 20, wherein the conductor consists of multiple spaced-apart conductive loops disposed at varying distances from an inner wall of said conduit.

22. The wear-detection sensor of claim 20, wherein the conductor is embedded in the insulating material.

23. The wear-detection sensor of claim 20, wherein the insulating material is urethane.

24. The wear-detection sensor of claim 20, further including signal processing circuitry mounted on the printed circuit board and connected to the conductor.

25. The wear-detection sensor of claim 20, wherein said body and conductor are substantially annular to conform to a tubular conduit.

26. The wear-detection sensor of claim 20, wherein said body is shaped as a tab insert adapted to span across a wall of said conduit.

27. The wear-detection sensor of claim 20, wherein said body is embedded in a protective lining of said conduit.

* * * * *